United States Patent [19]

Reng et al.

[11] Patent Number: 5,403,508
[45] Date of Patent: Apr. 4, 1995

[54] PEARLESCENT DISPERSIONS COMPRISING FATTY ACID GLYCOL ESTER AND NON-IONIC SURFACTANT

[75] Inventors: Alwin Reng, Kelkheim; Werner Skrypzak, Liederbach/Taunus; Walter Kunz, Hattersheim am Main, all of Germany

[73] Assignee: Hoechst AG, Frankfurt, Germany

[21] Appl. No.: 61,593

[22] Filed: May 13, 1993

[30] Foreign Application Priority Data

May 13, 1992 [DE] Germany .............. 42 15 732.3

[51] Int. Cl.$^6$ ............... C11D 1/825; C11D 17/00; A61K 7/06
[52] U.S. Cl. ............... 252/174.22; 252/173; 252/356; 252/DIG. 1; 252/DIG. 5; 252/DIG. 13; 424/70.31; 514/937
[58] Field of Search ............... 252/174.22, DIG. 13, 252/DIG. 1, DIG. 5, 356; 424/70; 514/937

[56] References Cited

U.S. PATENT DOCUMENTS

| | | | |
|---|---|---|---|
| 4,486,334 | 12/1984 | Horiuchi et al. | 252/312 |
| 4,620,976 | 11/1986 | Quack et al. | 424/70 |
| 4,654,163 | 3/1987 | Quack et al. | 252/312 |
| 4,654,207 | 3/1987 | Preston | 424/70 |
| 4,777,038 | 10/1988 | Scheuffgen | 424/70 |
| 5,017,305 | 5/1991 | Hoeffkes et al. | 252/311 |
| 5,019,376 | 5/1991 | Uick | 424/70 |
| 5,034,159 | 7/1991 | Tesmann et al. | 252/551 |
| 5,098,596 | 3/1992 | Balzer | 252/174.21 |
| 5,190,699 | 3/1993 | Hohn et al. | 252/557 |
| 5,213,792 | 5/1993 | Grundmann et al. | 424/70 |

FOREIGN PATENT DOCUMENTS

| | | |
|---|---|---|
| 0158174 | 10/1985 | European Pat. Off. . |
| 0300379 | 1/1989 | European Pat. Off. . |
| 0535693 | 4/1993 | European Pat. Off. . |
| 3843572 | 6/1990 | Germany . |
| 60-038309 | 2/1985 | Japan . |
| 92/13512 | 8/1992 | WIPO . |

*Primary Examiner*—Paul Lieberman
*Assistant Examiner*—A. Hertzog
*Attorney, Agent, or Firm*—Connolly and Hutz

[57] ABSTRACT

The present invention relates to nonionic, flowable pearlescent dispersions which comprise 5 to 30% by weight of a fatty acid glycol ester of the formula I as a pearlescence-forming agent, 0.1–20% by weight of a nonionic surfactant of the formula II and water in the amount lacking to make up 100% by weight.

20 Claims, 2 Drawing Sheets

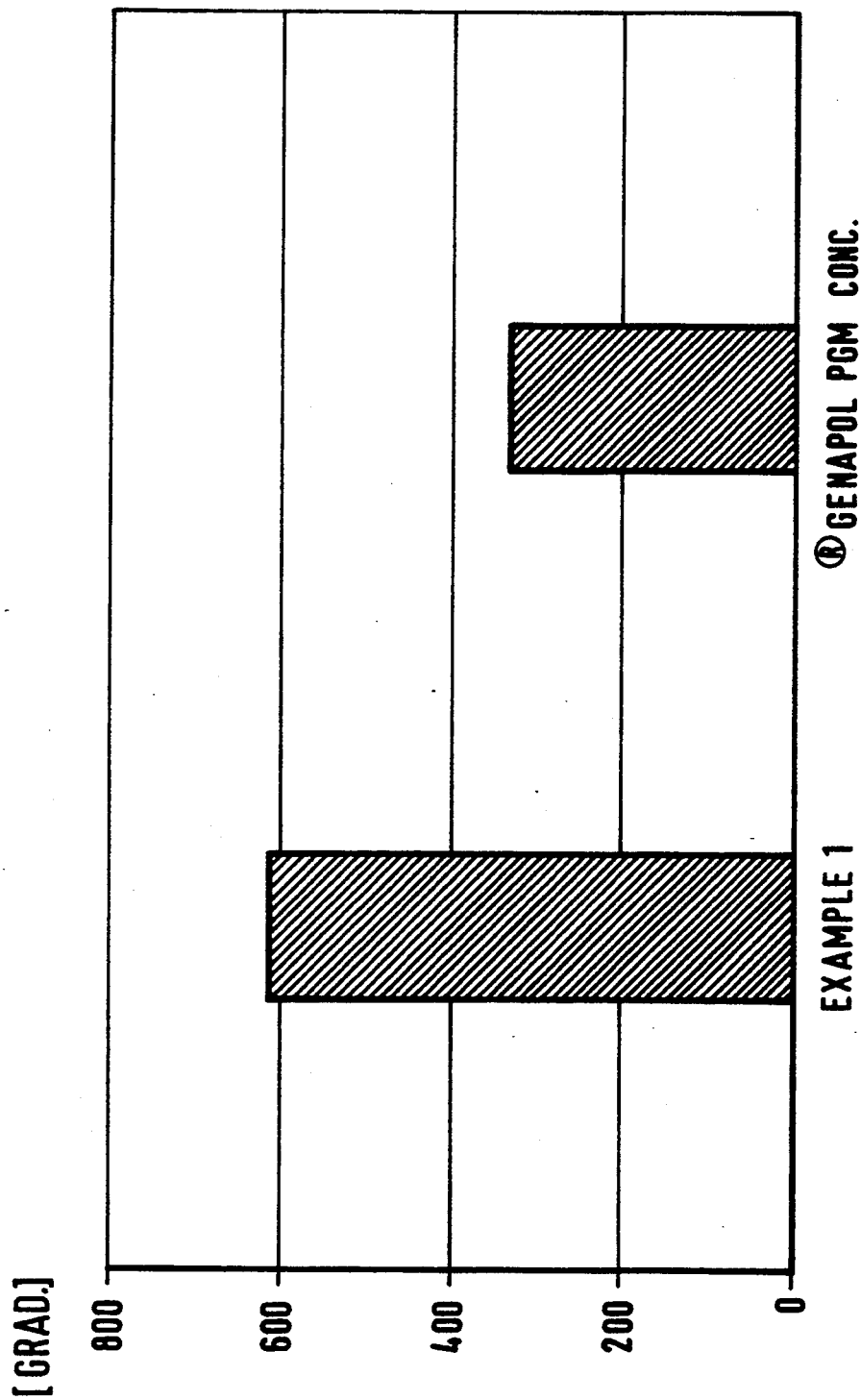

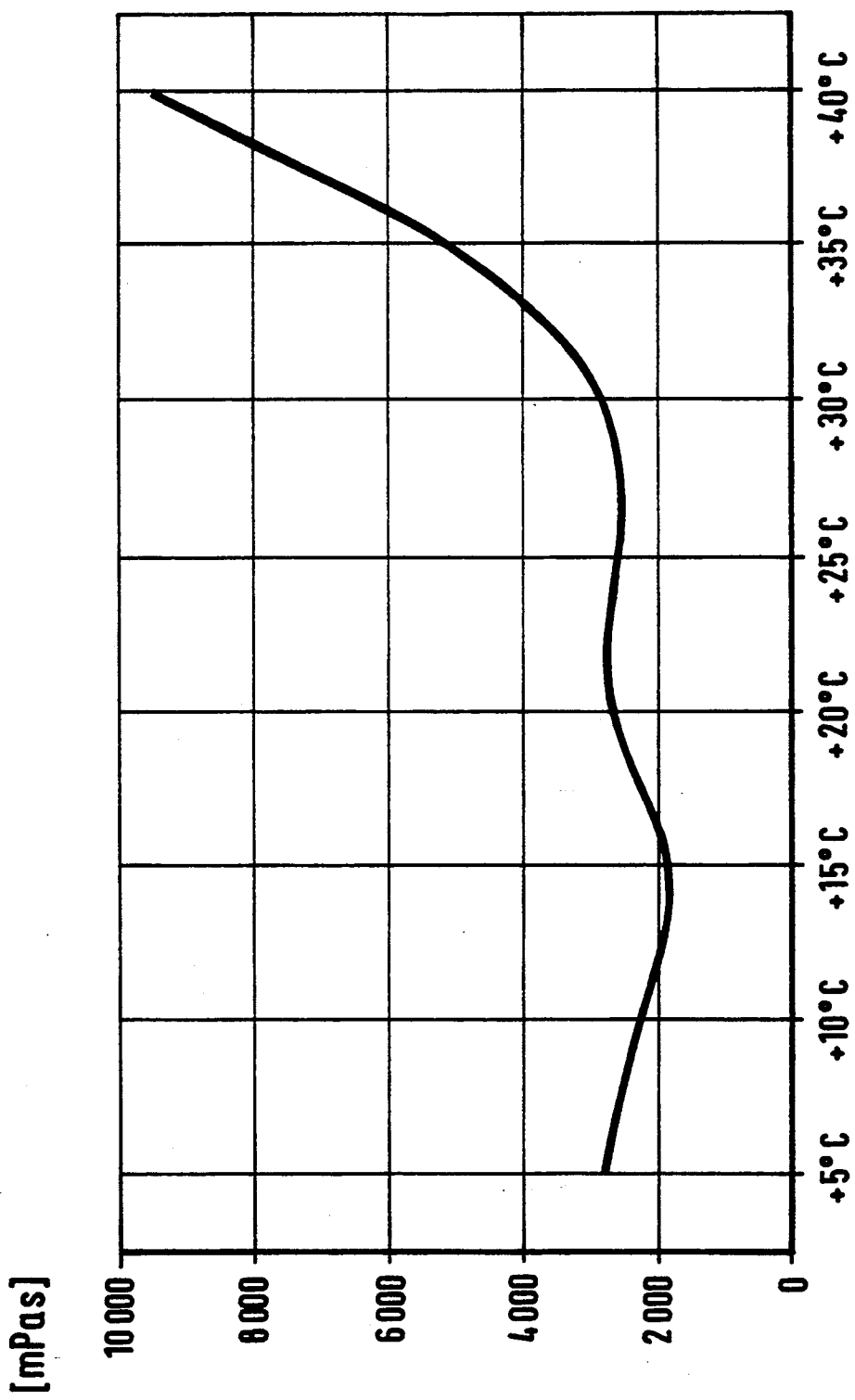

PEARLESCENT DISPERSIONS COMPRISING FATTY ACID GLYCOL ESTER AND NON-IONIC SURFACTANT

In the preparation of cosmetic hair and body cleansing agents, dishwashing agents and liquid washing and cleaning agents, substances which impart to the preparations mentioned a pearlescent-like appearance are often used to improve the visual aspect and therefore to increase the commercial value. Various substances are known for achieving such a pearlescent or silky luster effect, for example pulverulent naturally occurring substances, such as mica or fish scale, inorganic materials, such as bismuth oxychloride and titanium dioxide pigments, and furthermore metal salts of higher fatty acids, fatty acid glycol esters and fatty acid alkanolamides, as a mixture with other surfactants.

A fatty acid glycol ester in combination with a fatty acid alkanolamide is usually used as a pearlescence-imparting component for this purpose. In the preparation of washing and cleaning agents having a pearlescent effect for cosmetics and industry, these solid substances are traditionally dispersed in the surfactant phase by heating the batch to above the melting point of the substances mentioned. On cooling, these pearlescent-imparting components precipitate out as crystals and impart the desired pearlescent effect to the finished products.

Flowable pearlescent dispersions which essentially comprise fatty acid glycol esters, fatty acid alkanolamides, ionic surfactants, mono- or divalent metal salts and water are known from U.S. Pat. No. 4,620,976.

U.S. Pat. No. 4,654,163 describes nonionic, flowable pearlescent dispersions of fatty acid glycol esters, fatty acid alkanolamides, nonionic surfactants and water.

It has been found that when fatty acid alkanolamides are used, nitrosamines, which are a health hazard, can also be formed because of the residual amounts of secondary amines present. It has also been found that when the customary fatty acid alkanolamides are used, such as coconut fatty acid monoethanolamide, the formation occurs of relatively large crystals which tend to separate out to an increased extent and on the other hand bring about a low optical density, i.e. a low yield.

The object of the invention is to provide pearlescent dispersions which are free from fatty acid alkanolamides and nevertheless have the properties of the known pearlescent dispersions, such as low viscosity, good storage stability and excellent pearlescent effect.

The invention relates to nonionic, flowable pearlescent dispersions comprising 5–30% by weight of a fatty acid glycol ester of the formula I $$R^1-C(O)-(O-A)_m-O-X \qquad (I)$$

in which $R^1$ is a saturated or unsaturated hydrocarbon chain having 13–21 carbon atoms, A is a group of the formula $-C_2H_4-$ or $-C_3H_6-$, preferably $-C_2H_4-$, X is a hydrogen atom or a group of the formula $$R^5-C(O)-$$

$R^5$ is a saturated or unsaturated hydrocarbon chain having 13–21 carbon atoms, $R^1$ and $R^5$ independently of one another are identical or different, preferably identical, and m is a number from 1 to 10, preferably 1 to 3, 0.1–20% by weight of a nonionic surfactant of the formula II $$R^2-O-(A-O)_n-R^3 \qquad (II)$$

in which $R^2$ is a saturated or unsaturated hydrocarbon group having 8–30 carbon atoms, $R^3$ is a hydrogen atom or a group of the formula $$-CH_2-O-R^4$$

$R^4$ is a saturated or unsaturated hydrocarbon group having 1–10 carbon atoms, A and B independently of one another are a group of the formula $-C_2H_4-$ or $-C_3H_6-$ and n and p each independently are a number from 1 to 30, preferably 3 to 10, and water in the amount lacking to make 100% by weight.

The components required for the preparation of the pearlescent dispersions according to the invention and the use concentration are described below.

FIG. 1 shows that the Example 1 pearlescent agent has a considerably higher optical density than a commercially available product. FIG. 2 shows how the viscosity values of the Example 1 pearlescent agent vary with temperature.

Fatty acid glycol esters of the formula I and mixtures of these substances have proved to be suitable pearlescent-forming agents. The most favorable properties are shown by compounds in which $R^1$ is an alkyl radical having 15–17 carbon atoms, m=1 and X is a radical of the formula $R^5-C(O)-$, in which $R^5$ is an alkyl radical having 15–17 carbon atoms and $R^1$ and $R^5$ are identical. The use concentration of these fatty acid glycol esters is preferably 15 to 30% by weight, the optimum concentration being 20 to 25% by weight, based on the weight of the mixture.

Among the abovementioned nonionic surfactants corresponding to formula II, the following compounds and mixtures thereof have proved to be particularly favorable: compounds in which $R^2$ is an alkyl group having 10 to 18 carbon atoms, which is linear or branched, A is a group of the formula $-C_2H_4-$, n is a number from 5 to 20, p=0 and $R^3$ is a hydrogen atom. Likewise, compounds in which $R^2$ is an alkyl group having 10 to 18 carbon atoms, which is linear or branched, A and B independently of one another are a group of the formula $-C_2H_4-$ or $-C_3H_6-$ and n and p are each a number from 1 to 20, preferably 3 to 10.

The use concentration of these nonionic surfactants is preferably 5 to 15% by weight, based on the total weight.

The pearlescent dispersions according to the invention can comprise 5 to 40% by weight, preferably 20 to 30% by weight, based on the total weight of the mixture, of low molecular weight polyhydric alcohols and/or polyols. Examples of low molecular weight polyhydric alcohols are ethylene glycol, diethylene glycol, 1,2-propylene glycol, 1,3-propylene glycol, sorbitol, mannitol, xylitol and glycerol. Examples of polyols which may be mentioned are polyethylene glycols having molecular weights of between 200 and 800. Among the suitable low molecular weight polyhydric alcohols and polyols, polyethylene glycols having molecular weights of between 200 and 600, by themselves or in combination with 1,2-propylene glycol and/or glycerol, have proved to be particularly suitable.

In the context of the abovementioned use concentrations of the individual components of the formulae I and II, by observing the preparation conditions described below, optimum pearlescent dispersions which have the following advantageous properties are obtained:
  a) excellent flow properties, even at lower temperatures (+5° C.); this provides the possibility of continuous processing;
  b) nonionic build-up, therefore no chemical reaction with cationic surfactants;
  c) free from nitrosamine-forming amines or alkanolamides;
  d) no compulsory addition of preservatives.

It has been found that a bacteriostatic or else a bactericidal effect is achieved by addition of low molecular weight polyhydric alcohols and/or polyols, so that the addition of preservatives, which was previously customary, is not absolutely necessary.

The remaining amount to give 100% by weight of the mixture is made up with water. The water used is desalinated water.

In addition to the abovementioned constituents of fatty acid glycol ester, nonionic surfactant, water and, if appropriate, low molecular weight polyhydric alcohols and/or polyols, the pearlescent dispersions according to the invention can also comprise additives, if required, such as buffer substances, electrolytes and/or preservatives, such as benzoic acid or sorbic acid. The amount of these additives is between 0 and 1.0% by weight, and is preferably 0.3 to 0.4% by weight.

The following procedure is undertaken for preparation of the pearlescent dispersions according to the invention: The two components of the formulae I and II are initially introduced into a mixing vessel (tank which can be heated) and are melted by heating to about 76° C. An aqueous solution, likewise heated to 75° C., or a mixture comprising polyols or low molecular weight polyhydric alcohols is added to this melt, if appropriate, while stirring. The stirring speed is 10 to 100 revolutions per minute, depending on the batch and tank size. The dispersion formed is cooled to a final temperature of 20° to 30° C., while stirring. Cooling is effected at a rate under controlled conditions in order to achieve a constant reproducible pearlescent effect.

During the cooling operation, the component of the formula I starts to crystallize at about 50° to 60° C. and forms the desired pearlescent effect. The pH of the dispersions is in the range from 4 to 9, preferably in the range between 5 and 8.

The pearlescent dispersions according to the invention can be added to liquid hair and body cleansing agents, liquid dishwashing agents and liquid washing and cleaning agents at room temperature. This gives end products which have an excellent pearlescence. The amount of pearlescent dispersion required for this purpose is between 1 and 15, preferably 2 and 5% by weight. Since the pearlescent dispersion according to the invention has a comparatively low viscosity at temperatures above 5° C., there is the possibility of processing the dispersion with the aid of automatic pumping, metering and mixing units. This is of particular interest for the fully continuous preparation of pearlescence-containing finished products.

The preparation of the pearlescent dispersion according to the invention is illustrated by the following examples. The amounts data in each case relate to percentages by weight. "EO" is ethylene oxide and "PO" is propylene oxide.

PREPARATION EXAMPLES

Example 1

| | | |
|---|---|---|
| Monoethylene glycol distearate | | 23.0% |
| $C_{8/18}$-fatty alcohol + 8 EO | | 4.0% |
| $C_{8/18}$-fatty alcohol + 5 EO | | 4.0% |
| $C_{12/15}$-fatty alcohol + 4 EO + 4 PO | | 2.0% |
| Water, preservative (sorbic acid) | to | 100.0% |

Example 2

| | | |
|---|---|---|
| Monoethylene glycol distearate | | 18.0% |
| $C_{8/18}$-fatty alcohol + 8 EO | | 5.0% |
| $C_{8/18}$-fatty alcohol + 5 EO | | 3.0% |
| $C_{12/15}$-fatty alcohol + 6 EO + 4 PO | | 2.0% |
| Glycerol | | 24.0% |
| Water | to | 100.0% |

Example 3

| | | |
|---|---|---|
| Ethylene glycol monostearate | | 20.0% |
| $C_{10/12}$-fatty alcohol + 4 EO + 4 PO | | 2.0% |
| $C_{8/18}$-fatty alcohol + 6 EO | | 9.0% |
| Water, preservative (benzoic acid) | to | 100.0% |

Example 4

| | | |
|---|---|---|
| Triethylene glycol distearate | | 15.0% |
| $C_{12/15}$-fatty alcohol + 6 EO + 4 PO | | 3.0% |
| $C_{8/18}$-fatty alcohol + 6 EO | | 7.0% |
| Glycerol | | 15.0% |
| Polyethylene glycol 400 | | 10.0% |
| Water | to | 100.0% |

These pearlescent dispersions according to Examples 1–4 were tested according to the following criteria:
1. Evaluation of the pearlescent effect
2. Determination of the "optical density"
3. Viscosity or flow properties
4. Storage stability at temperatures higher and lower than room temperature
5. Preservative loading test The tests were carried out in comparison with a commercially available pearlescent agent corresponding to the following composition:

| | | |
|---|---|---|
| Monoethylene glycol distearate | | 10.0% |
| Coconut fatty acid monoethanolamide | | 10.0% |
| Lauryl diglycol ether-sulfate sodium salt | | 18.0% |
| Water, preservative, electrolytes | to | 100.0% |

The corresponding test methods and results are given below.

1. Pearlescent effect

The pearlescent effect was evaluated visually by classifications of dull to brilliant. The pearlescent concentrates corresponding to Examples 1–4 were first evaluated directly and 2% strength by weight dilutions in desalinated water were then prepared. The pearlescent dispersions according to the invention have a pronounced pearlescent effect which manifests itself in a high brilliance.

2. Optical density

The optical density, stated in scale divisions [SD], was tested photometrically in a dilution of 4.0 g/l of water with the aid of a turbidity meter (according to Dr. Lange). As FIG. 1 shows, Example 1 has a considerably higher optical density compared with a commercially available pearlescent agent, and therefore a better yield when used in finished products.

3. Viscosity or flow properties

The viscosity was determined with a Brookfield viscometer, type RVT at 20 revolutions per minute at 20° C. in a 2.0% strength by weight solution. FIG. 2 shows the viscosity values of the pearlescent concentrate corresponding to Example 1 at various temperatures. It can be seen that the pearlescent concentrate has very favorable flow properties at temperatures customary in practice, i.e. pumpability and easy processing at these temperatures is guaranteed.

4. Storage stability at higher and lower temperatures

The above pearlescent concentrates corresponding to Examples 1–4 were stored at −5° C. for three months and at +40° C. for six months. At the end of the storage experiments, no signs of instability, i.e. sedimentation, were to be found.

5. Preservative loading

The pearlescent concentrate corresponding to Example 2 was subjected to a preservative loading test. The concentrate has a bactericidal or bacteriostatic action, i.e. no multiplication of the microorganisms under the stated test conditions were found during the test period.

USE EXAMPLES

|  | % by weight |
|---|---|
| 1. Hair shampoo | |
| Coconut amidopropylbetaine, 30% strength in water | 18.0 |
| Acylamino polyglycol ether-sulfate magnesium salt, 30% strength in water | 20.0 |
| Lauryl alcohol + 3 EO | |
| Pearlescent concentrate according to Example 1 | 1.0 |
| Water | to 100.0 |
| 2. Shower bath | |
| Lauryl diglycol ether-sulfate sodium salt, 28% strength in water | 35.0 |
| Coconut fatty acid isethionate sodium salt | 7.0 |
| Sodium chloride | 2.5 |
| Pearlescent concentrate according to Example 3 | 3.0 |
| Water | to 100.0 |
| 3. Dishwashing agent | |
| Secondary alkanesulfonate, 30% strength | 70.0 |
| Lauryl triglycol ether-sulfate sodium salt, 28% strength | 20.0 |
| Lauryl alcohol + 3 EO | 3.0 |
| Pearlescent concentrate according to Example 4 | 2.5 |
| Water | to 100.0 |
| 4. Nonionic hair after-treatment agent | |
| Pearlescent concentrate according to Example 1 | 20.0 |
| ®Tylose H 4000 (cellulose ether) | 1.5 |
| Citric acid | 0.3 |
| Water | to 100.0 |

We claim:

1. A nonionic, flowable pearlescent dispersion comprising
(a) 5–30% by weight of fatty acid glycol ester of the formula I $$R^1\text{---}C(O)\text{---}(O\text{---}A)_m\text{---}O\text{---}X \quad (I)$$

in which
$R^1$ is a saturated or unsaturated hydrocarbon chain having 13–21 carbon atoms,
A is a group of the formula —$C_2H_4$— or —$C_3H_6$—,
X is a hydrogen atom or a group of the formula $$R^5\text{---}C(O)\text{---}$$

$R^5$ is a saturated or unsaturated hydrocarbon chain having 13–21 carbon atoms,
$R^1$ and $R^5$ independently of one another are identical or different,
and m is a number from 1 to 10,
(b) 0.1–20% by weight of a nonionic surfactant of the formula II $$R^2\text{---}O\text{---}(A\text{---}O)_n\text{---}(B\text{---}O)_p\text{---}R^3 \quad (II)$$

in which
$R^2$ is a saturated or unsaturated hydrocarbon group having 8–30 carbon atoms,
$R^3$ is a hydrogen atom or a group of the formula $$\text{---}CH_2\text{---}O\text{---}R^4$$

$R^4$ is a saturated or unsaturated hydrocarbon group having 1–10 carbon atoms,
A is a group of the formula —$C_2H_4$, B is a group of the formula —$C_3H_6$— and
n is a number from 1 to 30, p is a number from 0 to 30;
(c) 15 to 40% by weight of a low molecular weight polyhydric alcohol and/or a low molecular weight polyol wherein said polyhydric alcohol is selected from the group consisting of ethylene glycol, diethylene glycol, 1,2-propylene glycol, 1,3-propylene glycol, sorbitol, mannitol, xylitol and glycerol; and said polyol is polyethylene glycol having a molecular weight of between 200 and 800; and
(d) water in the amount lacking to make 100% by weight;
and whereby said dispersion is non-ionic and free from alkanolamides.

2. A pearlescent dispersion as claimed in claim 1, wherein, in formula I, $R^1$ is $C_{15}$—$C_{17}$-alkyl, X is a group of the formula $R^5$—C(O)—, where $R^5$ is $C_{15}$-$C_{17}$-alkyl, and m is one, and in formula II, $R^2$ is $C_{10}$-$C_{18}$-alkyl, $R^3$ is a hydrogen atom, n is 5 to 20 and p is zero.

3. The dispersion as claimed in claim 2, wherein A is —$C_2H_4$—.

4. The dispersion as claimed in claim 3, which comprises 20 to 25% by weight of compounds of the formula I and 5 to 15% by weight of the compounds of formula II.

5. The dispersion as claimed in claim 4, which comprises 20 to 30% by weight based on the total weight of the low molecular polyhydric alcohol and/or of the low molecular weight polyol.

6. The dispersion as claimed in claim 5, wherein said polyhydric alcohol and/or polyol is selected from the group consisting of 1,2-propylene glycol, glycerol and polyethylene glycols having molecular weights of between 200 and 600 or mixtures thereof.

7. The dispersion as claimed in claim 6, which further comprises 0.3 to 0.4% by weight of additives selected from the group consisting of benzoic acid, sorbic acid, electrolytes and buffer substances or mixtures thereof.

8. A pearlescence-containing product which comprises 2 to 5% by weight of the dispersion as claimed in claim 7.

9. The pearlescence-containing product as claimed in claim 8, wherein said product is selected from the group consisting of liquid hair cleansing agents, body cleansing agents and liquid dishwashing agents.

10. A pearlescence-containing product comprising 1 to 15% of the dispersion as claimed in claim 1.

11. The pearlescence-containing product as claimed in claim 10, wherein said product is selected from the group consisting of liquid hair cleansing agents, body cleansing agents and liquid dishwashing agents.

12. A pearlescent dispersion as claimed in claim 1, which comprises 15-30% by weight of compounds of the formula I and 5-15% by weight of compounds of the formula II, based on the total weight.

13. The dispersion as claimed in claim 12, which comprises 20 to 25% by weight of compounds of the formula I.

14. The dispersion as claimed in claim 1, wherein A is $—C_2H_4—$ and $R^1$ and $R^5$ are identical and m is 1.

15. The dispersion as claimed in claim 14, wherein n is a number from 3 to 10 and p is a number from 3 to 10.

16. The dispersion as claimed in claim 1, which comprises 20 to 30% by weight based on the total weight of the low molecular polyhydric alcohol and/or of the low molecular weight polyol.

17. The dispersion as claimed in claim 1, comprising 20 to 30% by weight of said polyhydric alcohol and/or polyol which is selected from the group consisting of 1,2-propylene glycol, glycerol and polyethylene glycols having molecular weights of between 200 and 600 or mixtures thereof.

18. The dispersion as claimed in claim 1, which further comprises 0 to 1% by weight of additives and wherein said additives are selected from the group consisting of buffer substances, electrolytes and preservatives or mixtures thereof.

19. A nonionic, flowable pearlescent dispersion consisting essentially of
(a) 5-30% by weight of a fatty acid glycol ester of the formula I

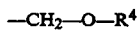

in which
$R^1$ is a saturated or unsaturated hydrocarbon chain having 13-21 carbon atoms,
A is a group of the formula $—C_2H_4—$ or $—C_3H_6—$,
X is a hydrogen atom or a group of the formula

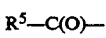

$R^5$ is a saturated or unsaturated hydrocarbon chain having 13-21 carbon atoms,
$R^1$ and $R^5$ independently of one another are identical or different,
and m is a number from 1 to 10,
(b) 0.1-20% by weight of a nonionic surfactant of the formula II

in which
$R^2$ is a saturated or unsaturated hydrocarbon group having 8-30 carbon atoms,
$R^3$ is a hydrogen atom or a group of the formula $—CH_2—O—R^4$ $R^4$ is a saturated or unsaturated hydrocarbon group having 1-10 carbon atoms,
A is a group of the formula $—C_2H_4$, B is a group of the formula $—C_3H_6—$ and
n is a number from 1 to 30, p is a number from 0 to 30;
(c) 15 to 40% by weight of a low molecular weight polyhydric alcohol and/or a low molecular weight polyol wherein said polyhydric alcohol is selected from the group consisting of ethylene glycol, diethylene glycol, 1,2-propylene glycol, 1,3-propylene glycol, sorbitol, mannitol, xylitol and glycerol; and said polyol is polyethylene glycol having a molecular weight of between 200 and 800; and
(d) water in the amount lacking to make 100% by weight;
and whereby said dispersion is non-ionic and free from alkanolamides.

20. A nonionic, flowable pearlescent dispersion comprising
(a) 5-30% by weight of fatty acid glycol ester of the formula I

in which $R^1$ is a saturated or unsaturated hydrocarbon chain having 13-21 carbon atoms,
A is a group of the formula $—C_2H_4—$ or $—C_3H_6—$,
X is a hydrogen atom or a group of the formula

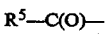

$R^5$ is a saturated or unsaturated hydrocarbon chain having 13-21 carbon atoms,
$R^1$ and $R^5$ independently of one another are identical or different,
and m is a number from 1 to 10,
(b) 0.1-20% by weight of a nonionic surfactant of the formula II

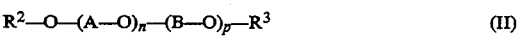

in which $R^2$ is a saturated or unsaturated hydrocarbon group having 8-30 carbon atoms,
$R^3$ is a hydrogen atom or a group of the formula $—CH_2—O—R^4$ $R^4$ is a saturated or unsaturated hydrocarbon group having 1-10 carbon atoms,
A is a group of the formula $—C_2H_4$, B is a group of the formula $—C_3H_6—$ and
n is a number from 1 to 30, p is a number from 0 to 30;
(c) 15 to 40% by weight of a low molecular weight polyhydric alcohol and/or a low molecular weight polyol having a molecular weight of between 62 and 800; and
(d) water in the amount lacking to make 100% by weight;
and whereby said dispersion is non-ionic and free from alkanolamides.

* * * * *